(12) United States Patent
Bartelmez et al.

(10) Patent No.: US 8,754,056 B2
(45) Date of Patent: Jun. 17, 2014

(54) ENHANCING VESSEL LESION HOMING AND REPAIR POTENTIAL OF STEM CELLS

(75) Inventors: Stephen H. Bartelmez, Sausalito, CA (US); Maria Grant, Gainesville, FL (US)

(73) Assignees: University of Florida Research Foundation, Inc., Gainesville, FL (US); BetaStem Therapeutics, Inc., San Francisco, CA (US)

(*) Notice: Subject to any disclaimer, the term of this patent is extended or adjusted under 35 U.S.C. 154(b) by 25 days.

(21) Appl. No.: 12/933,482

(22) PCT Filed: Mar. 19, 2009

(86) PCT No.: PCT/US2009/037625
§ 371 (c)(1), (2), (4) Date: Jan. 19, 2011

(87) PCT Pub. No.: WO2009/117553
PCT Pub. Date: Sep. 24, 2009

(65) Prior Publication Data
US 2011/0206688 A1   Aug. 25, 2011

Related U.S. Application Data

(60) Provisional application No. 61/038,164, filed on Mar. 20, 2008.

(51) Int. Cl.
*C12N 15/11* (2006.01)

(52) U.S. Cl.
USPC ...................................... 514/44 A

(58) Field of Classification Search
USPC ...................................... 514/44 A
See application file for complete search history.

(56) References Cited

U.S. PATENT DOCUMENTS

| | | | |
|---|---|---|---|
| 5,994,515 A | 11/1999 | Hoxie | |
| 6,627,191 B1 | 9/2003 | Bartelmez et al. | |
| 6,841,542 B2 * | 1/2005 | Bartelmez et al. | 514/44 A |
| 6,869,795 B1 | 3/2005 | Bartelmez et al. | |
| 2003/0109465 A1 | 6/2003 | Bartelmez et al. | |
| 2003/0180705 A1 * | 9/2003 | Murohara et al. | 435/2 |
| 2005/0002915 A1 * | 1/2005 | Atala et al. | 424/93.21 |
| 2005/0074435 A1 | 4/2005 | Casper et al. | |
| 2005/0276802 A1 | 12/2005 | Adams et al. | |
| 2006/0024287 A1 | 2/2006 | Glidden | |
| 2006/0104968 A1 | 5/2006 | Bookbinder et al. | |
| 2007/0036768 A1 | 2/2007 | Fraser et al. | |
| 2010/0034794 A1 * | 2/2010 | van der Strate et al. | 424/93.71 |

FOREIGN PATENT DOCUMENTS

WO   WO2005/018559   3/2005

OTHER PUBLICATIONS

"Expression of Smad7 in Mouse Eyes Accelerates Healing of Corneal Tissue after Exposure to Alkali," Saika et al. American Journal of Pathology, vol. 166, No. 5 May 2005.
Ruscetti, Francis W. et al., "Autocrine transforming growth factor-B regulation of hematopoiesis: many outcomes that depend on the context", 2005, Oncogene, vol. 24, pp. 5751-5763.
Bhatwadekar, Ahay D. et al., "Transient Inhibition of Transforming Growth Factor-B1 in Human Diabetic CD34+ cells Enhances Vascular Reparative Functions", Aug. 2010, Diabeter, vol. 59, pp. 2010-2019.

* cited by examiner

*Primary Examiner* — Brian Whiteman
(74) *Attorney, Agent, or Firm* — Timothy H. Van Dyke; Beusse, Wolter, Sanks, Mora & Maire, P.A.

(57) ABSTRACT

Disclosed herein are methods of enhancing repair of vascular lesions involving the administration of cells in which TGF-β expression and/or activity has been transiently blocked. Other methods involve the administration of a TGF-β blocking agent to a subject who has a vascular lesion or is at risk of developing a vascular lesion. Alternatively, a TGF-β blocking agent and treated cells are co-administered to a subject in need thereof.

9 Claims, 11 Drawing Sheets

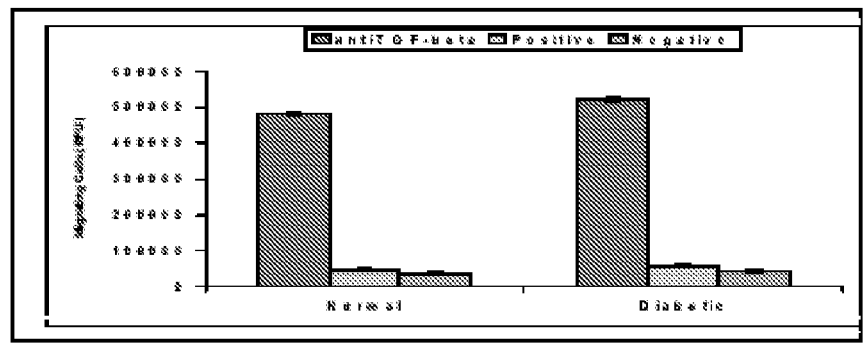
FIG. 3
FIG. 4
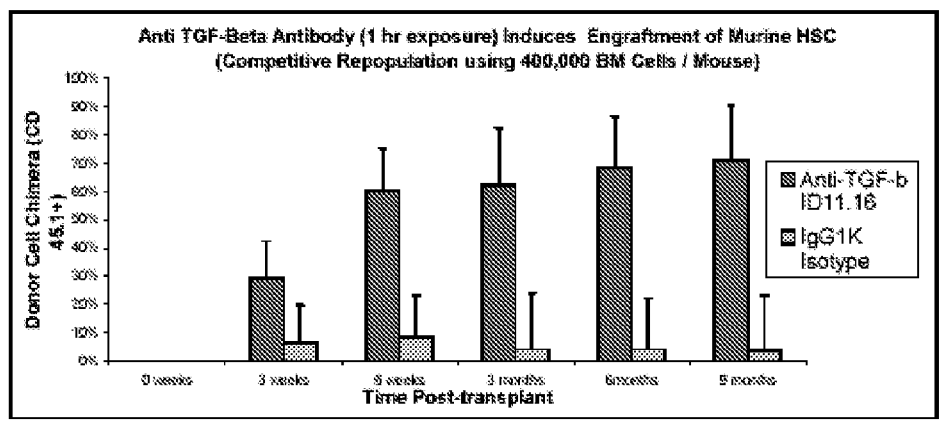

A

B

A

B

A

B (a)

(b)

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgttctgata gctgtacctc                                                 20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(15)
<223> OTHER INFORMATION: Inosine

<400> SEQUENCE: 2
gagggcggca tgnnngaggc                                                 20

US 8,754,056 B2

ENHANCING VESSEL LESION HOMING AND REPAIR POTENTIAL OF STEM CELLS

RELATED APPLICATIONS

This application claims priority to U. S. Ser. No. 61/038,164, filed on Mar. 20, 2008, which is incorporated herein in its entirety.

BACKGROUND

Circulating bone marrow (BM)-derived cells have been shown to play an important role in normal physiologic maintenance and repair of the body's vasculature with approximately 1-12% of endothelial cells at any one time being BM-derived (Schatteman, G. C. Adult bone marrow-derived hemangioblasts, endothelial cell progenitors, and EPCs, *Curr Top Dev Biol* 64, 141-80 (2004)). The ability to repair vascular damage could have a profound impact on diabetes induced complications. Diabetes affects 20 million Americans or about 7 percent of the population. Diabetic complications include heart disease, stroke, kidney failure, blindness, as well as nerve and peripheral vascular disease that can lead to lower limb amputations. Furthermore, preventing diabetic complications could save $2.5 billion annually. Recent evidence suggests that hematopoietic stem cells (HSC) differentiate into vascular structures as well as into all hematopoietic cell lineages and this has spawned the era of cellular therapies for vascular insufficency. These therapies are now attempting to replace traditional approaches such as stents, angioplasty or vessel grafts to alleviate tissue ischemia (Losordo, D. W. & Dimmeler, S. Therapeutic angiogenesis and vasculogenesis for ischemic disease: part II: cell-based therapies, *Circulation* 109, 2692-7 (2004)). BM derived cells can differentiate into endothelial cells and these cells are thought to be important in processes such as vasculogenesis and vascular repair. The entire diabetic endothelium suffers damage as a result of oxidative stress and hyperglycemic. Injured macrovasculature endothelium, if not repaired, leads to a propensity for arteriosclerosis. With regard to the microvasculature, this same endothelial damage results in capillary damage in the heart, nerves, skin and retina (Kugler, C. F. & Rudofsky, G. The challenges of treating peripheral arterial disease, *Vasc Med* 8, 109-14 (2003)).

In capillaries, a defect in the endothelial progenitor cells (EPCs) could prevent reparation of endothelial injury early on leading to tissue ischemia. In the macrovasculature this same inability to repair the endothelium results in an increase in cytokines and up regulation of adhesion molecules with an influx of lipoprotein, monocytes, and T cells; initiating the atherosclerotic lesion (Ross, R., Glomset, J. & Harker, L. Response to injury and atherogenesis, *Am J Pathol* 86, 675-84 (1977)). Thus the cause of diabetic microvascular and macrovascular dysfunction may be the same; lack of EPC repair of the endothelium.

TGF-β1 is a pleiotropic regulator of all stages of hematopoiesis (Ruscetti, F. W. & Bartelmez, S. H. Transforming growth factor beta, pleiotropic regulator of hematopoietic stem cells: potential physiological and clinical relevance, *Int J Hematol* 74, 18-25 (2001)). Furthermore, HSC themselves express and secrete active forms of TGF-β (Ruscetti, F. W., Akel, S. & Bartelmez, S. H. Autocrine transforming growth factor-beta regulation of hematopoiesis: many outcomes that depend on the context. *Oncogene* 24, 5751-63 (2005)). The three mammalian isoforms (TGF-β1, 2 and 3) have distinct but overlapping effects on hematopoiesis, but TGF-β1 is the predominate expressed gene in HSC. Depending on the differentiation stage of the target cell, the local environment and the concentration of TGF-β, in vivo or in vitro, TGF-β can be pro- or anti-proliferative, pro- or anti-apoptotic, induce or inhibit differentiation, and can inhibit or increase terminally differentiated cell function. Described herein for the first time is the inventors' discovery that transient neutralization of endogenous TGF-β in HSC dramatically increases the vascular reparative potential of circulating HSC.

BRIEF DESCRIPTION OF THE DRAWINGS

FIG. 3 shows a graph demonstrating that human CD34+ cells treated with anti-TGF-β had enhanced migration in response to the stem/progenitor cell homing factor SDF-1, over control treated cells.

FIG. 4 shows a graph demonstrating that anti-TGF-β cells produced a larger percentage of donor cell chimeras compared to control treated cells.

DETAILED DESCRIPTION

Figure 1:
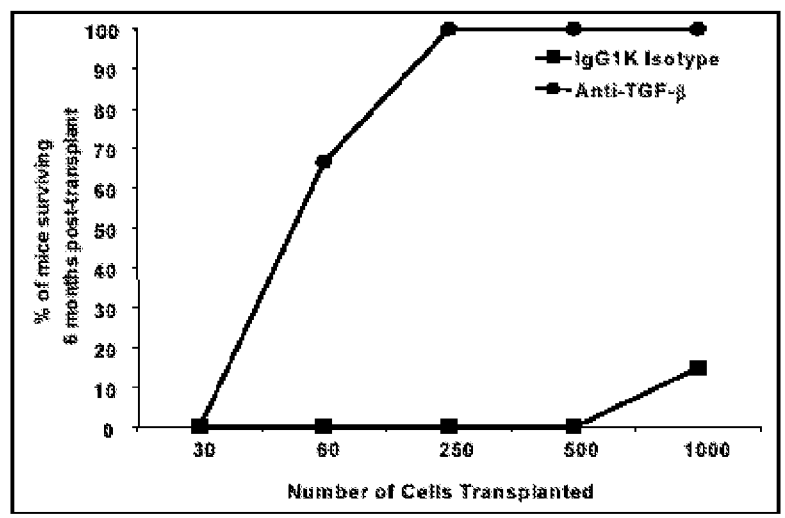
FIG. 1 shows a graph demonstrating that mice transplanted with anti-TGF-β treated cells had an increased percentage survival compared to control treated cells.

The present invention is based on and is a further development of the inventors' discovery that exposure of HSCs to TGF-β blockade just prior to transplantation accelerates engraftment of HSC as well as increases their ability to rescue a lethally irradiated mouse from hematopoietic failure. The inventors believe that treatment of stem cells, particularly, HSCs increases their homing ability to vascular lesions, and thus increases the reparative potential of the treated HSCs. Endothelial precursor cells have the ability to promote vascular repair. The approach outlined herein of blocking TGF-β transiently in EPCs enhances the ability of such cells to proliferate, migrate and home into areas of injury. This temporary blockade of TGF-β results in the release of these cells from growth inhibition. These typically express high levels of TGF-β to keep these cells in their naturally quiescent state as stem cells. This treatment enhances the vascular repair potential, which is applicable to all vessels. According to one embodiment of the invention, repair of coronary vessels following myocardial infarction is achieved by administration of treated stem cells. In another embodiment, cerebral vessels are repaired following stroke. In addition, injured peripheral vascular beds are repaired by administration of treated cells.

One embodiment of the subject invention pertains to a method of treating vascular lesions in a subject in need thereof. The term subject as used herein refers to a human or non-human mammals. Non-human mammals include, but are not limited to, rodents such as rats and mice, cats, dogs, horses, cattle, goats, sheep or pigs. The method involves procuring hematopoietic stem cells from the subject to obtain procured hematopoietic stem cells. The procured hematopoietic stem cells are treated, ex vivo, by blocking activity of TGF-β in the cells. Examples of TGF-β blocking agents are disclosed in U.S. Pat. Nos. 6,869,795, 6,841,542 and 6,627,191. In a specific embodiment, TGF-β is blocked by subjecting procured cells with an antibody specific to TGF-β1, TGF-β2 or TGF-β3. Specific examples of antibodies useful in accordance with the teachings herein are taught in U.S. Pat. No. 6,627,191. In another specific embodiment, TGF-β is blocked by an antisense oligomer. Specific examples of antisense oligomers useful in accordance with the teachings herein are disclosed in U.S. Pat. Nos. 6,869,795 and 6,841,542.

As provided by the methods of the invention herein, the term "administering", "administer" or "administration" with respect to delivery of cells to a subject refers to injecting one or a plurality of cells with a syringe, inserting the stem cells with a catheter or surgically implanting the stem cells. In certain embodiments, the stem cells are administered into a body cavity fluidly connected to a target tissue. In other embodiments, the stem cells are inserted using a syringe or catheter, or surgically implanted directly at the target tissue site. In other embodiments, the stem cells are administered systemically (e.g., parenterally). In other specific examples, stem cells are administered by intraocular delivery, intramuscular delivery, subcutaneous delivery or intraperitoneal delivery.

As provided by the methods of the invention herein, the term "administering", "administer" or "administration" with respect to delivery of a TGF-β blocking agent to a subject refers to parenteral administration, intraperitoneal, intramuscular, intraocular administration including transcleral administration and intravitreal injection; transdermal administration, oral administration, intranasal administration, direct delivery to a target site or delivery to a body cavity in fluid communication with a target site As used herein, the term "enhancing repair of a vessel lesion" refers to an improvement in the state of a lesion in blood vessels in the body. Improvement in the state may involve partial or full healing of the lesion. Healing of the may include remodeling of the wounded tissue at the lesion and surrounding tissue.

As used herein, the terms "antisense oligonucleotide" and "antisense oligomer" are used interchangeably and refer to a sequence of nucleotide bases and a subunit-to-subunit backbone that allows the antisense oligonucleotide or oligomer to hybridize to a target sequence in an RNA by Watson-Crick base pairing, to form an RNA:oligomer heteroduplex within the target sequence. The oligomer may have exact sequence complementarity to the target sequence or near complementarity. Such antisense oligomers may block or inhibit translation of the mRNA containing the target sequence, or inhibit gene transcription, may bind to double-stranded or single stranded sequences, and may be said to be "directed to" a sequence with which it hybridizes.

The term "coadministering" or "concurrent administration", when used, for example with respect to TGF-β blocking agent and a sample of treated cells, refers to administration of the agent and the cells such that both can simultaneously achieve a physiological effect. The agent and the cells, however, need not be administered together. In certain embodiments, administration of one can precede administration of the other, however, such coadministering typically results in both agent and cells being simultaneously present in the body (e.g. in the plasma) at a significant fraction (e.g. 20% or greater, preferably 30% or 40% or greater, more preferably 50% or 60% or greater, most preferably 70% or 80% or 90% or greater) of their maximum serum concentration for any given dose.

FIG. 1 shows one of a series of experiments in which 10-12 mice per group were transplanted with an increasing number of highly purified LTR-HSC in the absence of "support marrow. "Support marrow" provides a mechanism of rapid repopulation in which donor platelets and neutrophils can be generated within the first 1.5 weeks post transplant thus effecting a hematopoietic rescue. This temporary blockade of TGF-β in LTR-HSC induced survival in 60-100% of mice that received only 60-250 LTR-HSC per mouse. LTR-HSC treated with isotype antibody induced only 10% survival and only at the highest cell dose tested (1000 LTR-HSC per mouse). Thus, these studies uncover a profound effect that transiently blocking TGF-β (2-4 days) has on promoting engraftment and proliferation of LTR-HSC.

In further studies, the ability of LTR-HSC(CD45.1 congenic) to compete with other stem cells in the support marrow (CD45.2 congenic) was examined. FIG. 4 depicts the striking difference in donor cell repopulation after a brief treatment with anti-TGF-β antibody. LTR-HSC purified from B6SJL mice (CD45.1$^+$) were treated with anti-TGF-β antibody in PBS for 1-3 hours then transplanted into lethally irradiated (950 rads) C57Bl6 (CD45.2) mice along with 400,000 support marrow (unfractionated bone marrow support/competitor cells (CD45.2). The white bars (±S.D.) show a relatively low engraftment of control IgG1K isotype antibody-treated LTR-HSC, which is similar to that observed with untreated LTR-HSC (not shown). In contrast, the filled bars show the engraftment mediated by 100 LTR-HSC treated with anti-TGF-β antibody for 1-2 hours. These LTR-HSC rapidly engrafted after intravenous transplant to produce greater than 30% donor cells by three weeks with sustained engraftment of 60-70% for more than nine months. The early engraftment was predominantly donor neutrophils followed by B-cells and then T-cells by 1.5 months. Thus, the blockade of endogenous TGF-β in LTR-HSC induced not only rapid repopulation but also a durable donor cell graft. Therefore, the repopulating donor HSC retained their long-term repopulating ability as well as generated high levels of short-term repopulating HSC that are actually responsible for hematopoietic reconstitution of the differentiated cells.

Figure 2:
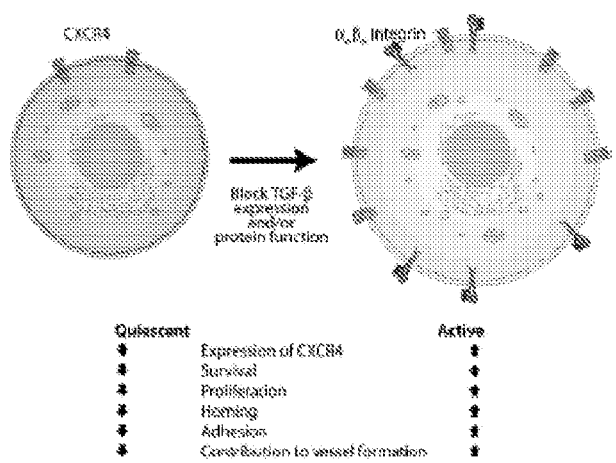
FIG. 2 represents a rendering of a cell and the effects of blocking TGF-β.

Without being bound to any particular theory, it is the inventors' belief that one of the mechanisms involved in the increased marrow engraftment potential of TGF-β blockade on HSCs may involve homing to the marrow or sites of vascular damage by increased expression of certain receptors/factors, as shown in FIG. 2. FIG. 3 shows human CD34$^+$ cell migration after pre-treatment with anti-TGF-β antibody or non-immune isotype control antibody. Cells were exposed to the antibody for one hour and then loaded into a Boyden chamber. SDF-1, the principal stem/progenitor cell homing factor, was used as the chemotaxis effector. Blockade of TGF-β ligand clearly results in enhanced migration in response to SDF-1. Data are mean±S.D. of triplicate wells. P values are against untreated cells exposed to basal media alone, i.e., with no migratory signal.

In another embodiment, hematopoietic stem cells may be obtained from a patient in need of transplantation, (e.g., a patient having a stroke or myocardial infarction event, a patient suffering from CNV, a patient suffering from atherosclerosis, a diabetic patient, or any other patient having a vessel lesion or risk of vessel lesion); enriched, treated in vitro (ex vivo) using the methods described herein, and returned to the patient.

In practicing a specific embodiment of the invention, hematopoietic stem cells may be treated in vitro (ex vivo) with one or more oligonucleotide antisense to a nucleic acid sequence that is preferentially expressed in stem cells, followed by administration to a subject. The subject may be the same individual from whom the stem cells were obtained (autologous transplantation) or a different individual (allogeneic transplantation). In allogeneic transplantation, the donor and recipient are matched based on similarity of HLA antigens in order to minimize the immune response of both donor and recipient cells against the other.

In one aspect, the invention is directed to methods of modifying the development of hematopoietic stem cells, by obtaining a population of HSCs and exposing them ex vivo to one or more nuclease-resistant antisense oligomers having high affinity to a complementary or near-complementary nucleic acid sequence preferentially expressed in stem cells. In another aspect, a population of HSCs is exposed to an anti-TGF-β antibody.

In one aspect, once extracted and enriched, stem cells, e.g., HSC, may be cultured ex vivo in the presence of one or more cytokines and one or more antisense oligomers and/or antibodies described herein. Such an antisense oligomer, and/or anti anti-TGF-β-treated hematopoietic stem cell composition finds utility in repairing, enhancing repair of vascular lesions.

Examples of cytokines for such ex vivo culture include, but are not limited to, IL-3, IL-6, SCF and TPO. A hematopoietic stem cell population for use in the methods of the invention is typically both human and allogeneic, or autologous.

Exemplary antisense oligomers target one or more of an EVI-1 zinc finger gene, a serum deprivation response (SDR) gene, a multimerin gene, a tissue transglutaminase gene, an FE65 gene, a RAB27 gene, a Jagged2 gene, a Notch1 gene, a Notch2 gene and a Notch3 gene.

Once a large number of cells, i.e., cells of a particular lineage, are obtained, the cells can be used immediately or frozen in liquid nitrogen and stored for long periods of time, using standard conditions, such that they can later be thawed and used, e.g., for administration to a patient. The cells will usually be stored in 10% DMSO, 50% fetal calf serum (FCS), and 40% cell culture medium.

In another aspect, the invention is directed to methods of modifying the development of stem cells in vivo in a patient in need thereof, by administering to the patient a therapeutically effective amount of an antisense oligonucleotide-containing composition, where the antisense oligomer modulates the expression of a gene product preferentially expressed in stem cells.

Such in vivo antisense oligomer administration may also be effective to improve the therapeutic outcome of the subject by effecting an enhancement of repair potential of endogenous untreated stem cells, or stem cells which have undergone, ex vivo, treatment and then administered to the subject.

In one example, the antisense oligonucleotide composition is administered at a concentration and for a period sufficient to increase the It will be understood that in vivo administration of such an antisense oligomer to a subject using the methods of the invention can provide a means to increase the population of lineage committed progenitor cells and their progeny in the peripheral circulation of the subject, and/or effect a slowing or diminution of the growth of cancer cells or a solid tumor, or a reduction in the total number of cancer cells or total tumor burden, dependent upon, (I) the duration, dose and frequency of antisense administration, (2) the one or more antisense oligomers used in the treatment; and (3) the general condition of the subject.

It is appreciated that any methods which are effective to deliver the TGF-β blocking agent to hematopoietic stem cells or to introduce the agent into the bloodstream are also contemplated.

Transdermal delivery of TGF-β blocking agent may be accomplished by use of a pharmaceutically acceptable carrier adapted for e.g., topical administration. One example of morpholino oligomer delivery is described in PCT patent application WO 97/40854, incorporated herein by reference.

In one specific embodiment, the TGF-β blocking agent, contained in a pharmaceutically acceptable carrier, and delivered orally. In a further aspect of this embodiment, a TGF-β blocking agent is administered at regular intervals for a short time period, e.g., daily for two weeks or less. However, in some cases the TGF-β blocking agent is administered intermittently over a longer period of time.

Typically, one or more doses of TGF-β blocking agent are administered, generally at regular intervals for a period of about one to two weeks. Preferred doses for oral administration are from about 1 mg agent/patient to about 25 mg oligomer/patient (based on an adult weight of 70 kg). In some cases, doses of greater than 25 mg blocking agent patient may be necessary. For IV administration, the preferred doses are from about 0.05 mg agent/patient to about 10 mg agent/patient (based on an adult weight of 70 kg).

The antisense compound is generally administered in an amount sufficient to result in a peak blood concentration of at least 200-400 nM blocking agent.

In one example, the method comprises administering to a subject, in a suitable pharmaceutical carrier, an amount of an antisense agent effective to inhibit expression of a nucleic acid target sequence of interest.

It follows that a blocking agent composition may be administered in any convenient vehicle, which is physiologically acceptable. Such blocking agent composition may include any of a variety of standard pharmaceutically accepted carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration In some instances liposomes may be employed to facilitate uptake of the blocking agentinto cells. (See, e.g., Williams, 1996; Lappalainen, et al., 1994; Uhlmann, et al., 1990; Gregoriadis, 1979.) Hydrogels may also be used as vehicles for antisense oligomer administration, for example, as described in WO 93/01286. Alternatively, the blocking agent may be administered in microspheres or microparticles. (See, e.g., Wu and Wu, 1987).

Sustained release compositions are also contemplated within the scope of this application. These may include semipermeable polymeric matrices in the form of shaped articles such as films or microcapsules.

It will be understood that the effective in vivo treatment regimen of the blocking agent in the methods of the invention will vary according to the frequency and route of administration as well as the condition of the subject under treatment. Accordingly, such in vivo therapy will generally require monitoring by tests appropriate to the condition being treated and a corresponding adjustment in the dose or treatment regimen in order to achieve an optimal therapeutic outcome.

The efficacy of a given therapeutic regimen involving the methods described herein, may be monitored, e.g., by conventional FACS assays for the phenotype of cells in the circulation of the subject under treatment in order to monitor changes in the numbers of cells of various lineages (e.g., lineage committed progenitor cells and their progeny) in the peripheral circulation of the subject in response to such treatment.

Phenotypic analysis is generally carried out using monoclonal antibodies specific to the cell type being analyzed, e.g., neutrophils, platelets, lymphocytes, erthryrocytes or monocytes. The use of monoclonal antibodies in such phenotypic analyses is routinely employed by those of skill in the art for cellular analyses. Monoclonal antibodies specific to particular cell types are commercially available.

Hematopoietic stem cells are characterized phenotypically as detailed above. Such phenotypic analyses are generally carried out in conjunction with biological assays for each particular cell type of interest, for example (1) hematopoietic stem cells (LTCIC, cobblestone forming assays, and assays for HPP-CFCs), (2) granulocytes or neutrophils (clonal agar or methyl cellulose assays wherein the medium contains G-CSF or GM-CSF), (3) megakaryocytes (clonal agar or methyl cellulose assays wherein the medium contains TPO, IL-3, IL-6 and IL-11), and (4) erythroid cells (clonal agar or methyl cellulose assays wherein the medium contains EPO and SCF or EPO, SCF and IL-3).

It will be understood that the exact nature of such phenotypic and biological assays will vary dependent upon the condition being treated and whether the treatment is directed to enhancing the population of hematopoietic stem cells or the population of cells of a particular lineage or lineages.

In cases where the subject has been diagnosed as having a particular type of lesion, the status of the lesion is also monitored using diagnostic techniques appropriate to the type of lesion under treatment to determine if repair of the lesion has progressed.

Example 1

Blockade of Endogenous TGF-β1 in Human CD34$^+$ Cells by Anti-TGF-β-PMO Promotes Survival of EPC in the Absence of Growth Factors For this study, AVI-Biopharma assembled morpholinos from five different subunits (including inosine to increase solubility), with each subunit joined to a six membered morpholino ring. Individual subunits were assembled in the desired order by non-ionic phosphorodiamidate inter-subunit linkages. The design of PMO conferred a unique advantage of specificity for the TGF-β1 inhibition with essentially no off-target effects. Initial studies utilized PMO-FITC conjugates to directly measure PMO uptake in highly enriched murine HSC and showed that PMO was taken up by HSC and plateaued after overnight ex vivo incubation (data not shown). Similarly, examination of the half-life of PMO in human lymphocytes was found to be approximately 2-4 days (data not shown).

Figure 5:
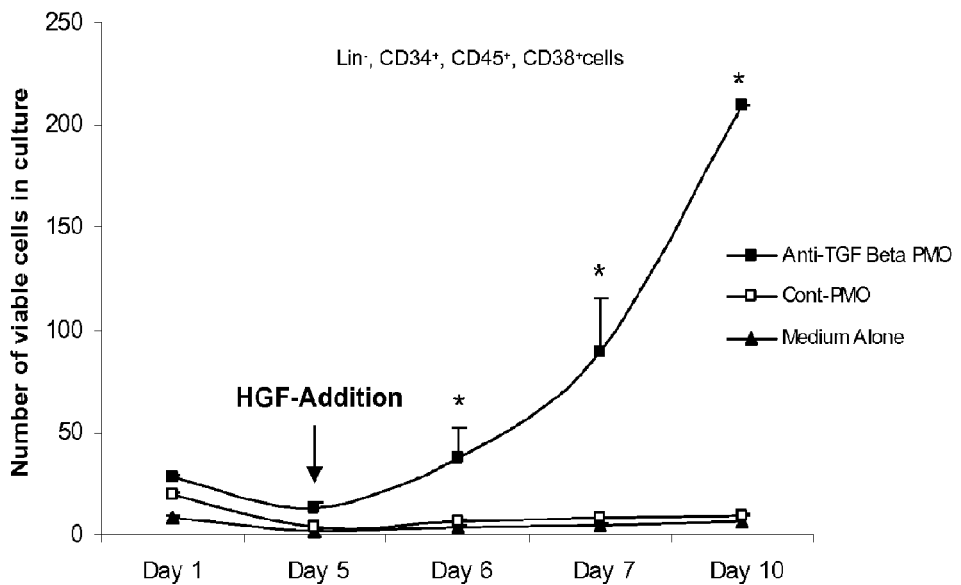
FIG. 5: Effect of TGF-β1-PMO blockade in $CD34^+$ subsets: survival in the absence of growth factors and subsequent proliferation induced by addition of HGF. (A) Survival of sorted $lin^-CD34^+CD45^+CD38^+$ umbilical cord blood cells (~99% of $CD34^+$ cells) in the absence of growth factors showing numbers of viable cells in culture over time. Cells (10 cells per well, x8 replicate wells) were sorted directly into round-bottom wells containing 10% FBS/10% HS/IMDM (medium alone) or 40 ug/ml TGF-β1-PMO or 40 ug/ml control-PMO. On day 5, HGF were added to the wells (final concentrations 20 ng/ml Tpo, 50 ng/ml SCF, 50 ng/ml IL-3, 20 ng/ml IL-6) to detect cells that survived during the first 5 days period. (B) Survival of sorted $line^-CD34^+CD45^+CD38^-$ umbilical cord blood cells (~1% of $CD34^+$ cells) in the absence of growth factors showing numbers of viable cells in culture over time, as described above.
Figure 5:
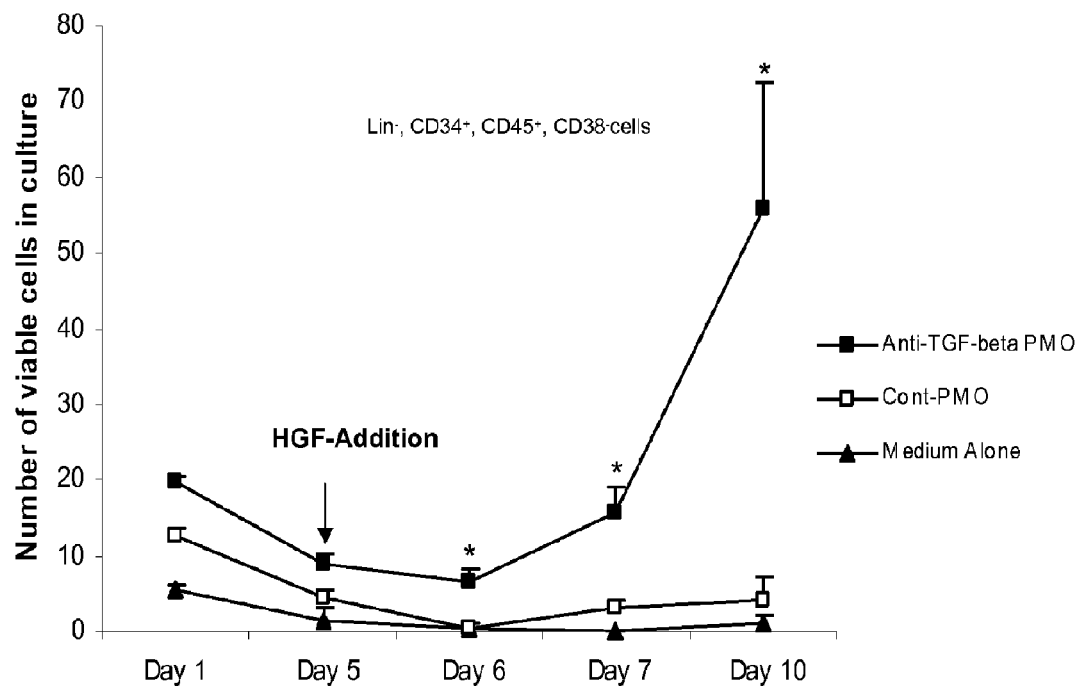

Two discrete cord blood stem cell populations, lin⁻CD34⁺CD38⁺ (FIG. 5A) or lin⁻CD34⁺CD38⁻ (FIG. 5B), in addition to lin⁻CD34⁺ cells from peripheral blood and bone marrow (FIG. 6A) were either treated with PMO containing medium or not. After 5 days, all cells received growth factors (Tpo, SCF, IL-3, IL-6) to detect live, growth factor responsive cells and their proliferative potential after 14 days was determined. By day 14, cells exposed to 20-300 μg/mL of anti-TGF-β-PMO typically formed macro colonies (>100,000 cells) after the addition of growth factors (FIG. 5). However, anti-TGF-β-PMO at 40 μg/mL resulted in the greatest cell survival.

Figure 6:
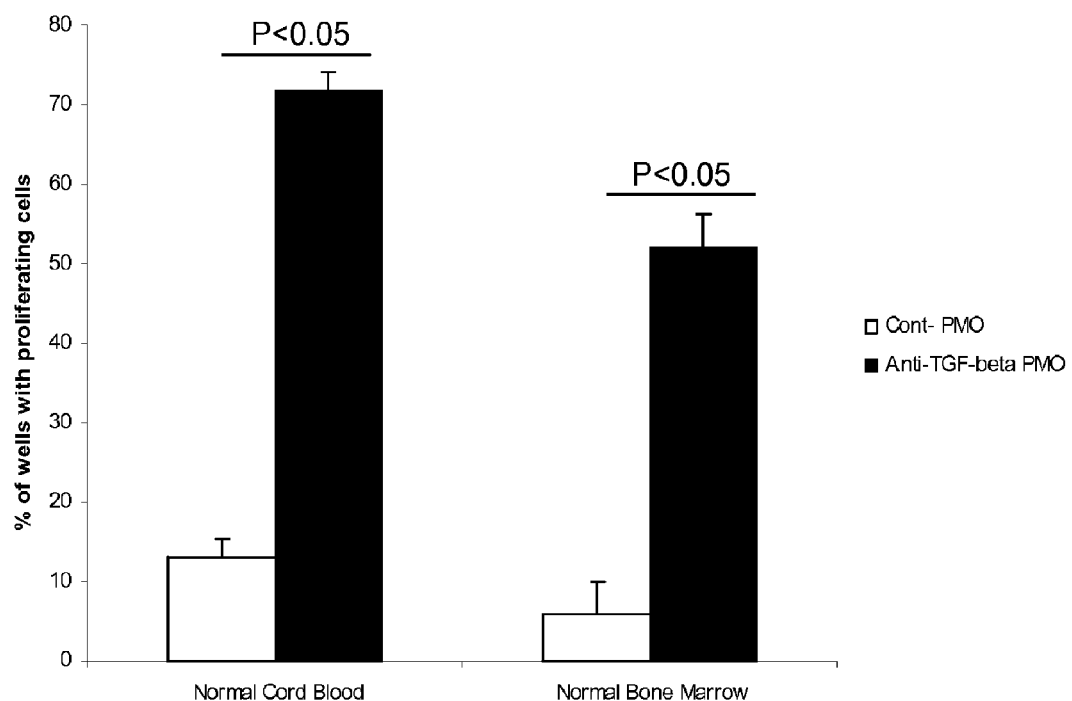
FIG. 6: TGF-β1-PMO treatment of HSC increases and Subsequent proliferation induced by addition of HGF. Under similar conditions to that discussed for FIG. 5, $CD34^+$ cells from normal human bone marrow or umbilical cord blood (C), human normal or diabetic peripheral blood (D), (10 cells per well, x8 replicate wells) were treated with TGF-β1-PMO or control-PMO (40 ug/ml) and results are expressed as % of wells that exhibited significant proliferation (>1000 cells per well) 5 days after growth factor addition.
Figure 6:
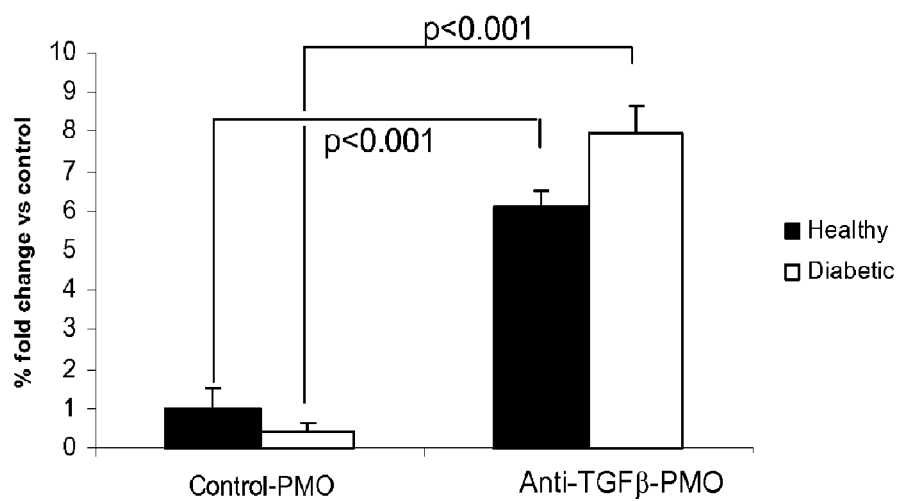

BM-derived cells responded in a manner similar to cord blood-derived cells with anti-TGF-β-PMO treatment, showing increased proliferation compared to cells treated with control-PMO (FIG. 6A). When peripheral blood CD34⁺ cells from diabetics and age- and sex-matched controls were exposed to anti-TGF-β-PMO, (FIG. 6B), cells responded with enhanced proliferation in the absence of growth factors compared to cells treated with control-PMO.

Example 2

Blockade of Endogenous TGF-β1 by Anti-TGF-β-PMO Accelerates Migration of Human CD34⁺ EPCs to SDF-1

Figure 7:
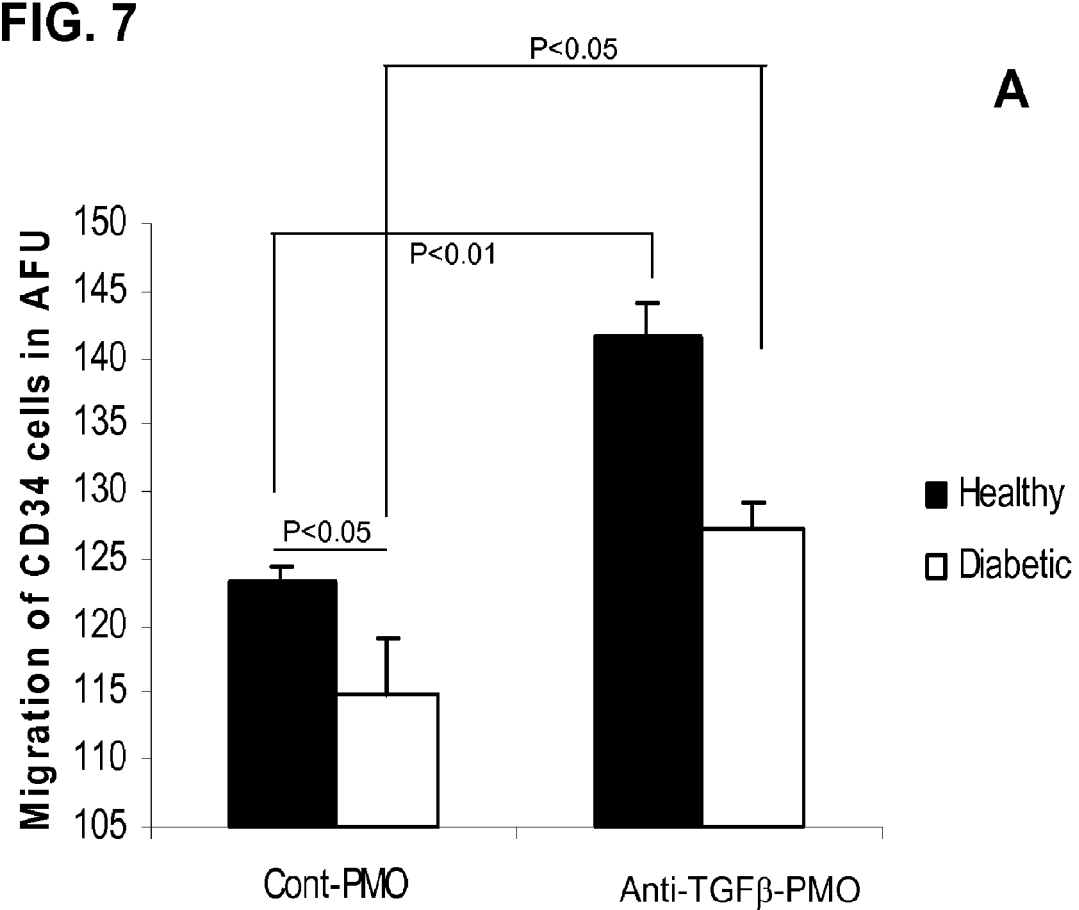
FIG. 7: Effects of PMOs on migration of non-diabetic and diabetic $CD34^+$ EPCs in response to SDF-1 (100 nM) in Boyden chamber assay: Migration of diabetic cells was significantly lower compared to non-diabetic cells when treated with control-PMO ($P<0.05$). Treatment with anti-TGF-β-PMO enhanced migration to SDF-1 in both groups ($P<0.01$ non-diabetic; $P<0.05$ diabetic).

Migratory potential of HSC is vital for their mobilization from bone marrow into circulation and from the circulation to areas of vascular repair. SDF-1 is the key cytokine that stimulates migration of CD34⁺ EPCs into sites of ischemia (Urbich C, Aicher A, Heeschen C, et al. Soluble factors released by endothelial progenitor cells promote migration of endothelial cells and cardiac resident progenitor cells. J Mol Cell Cardiol. 2005; 39:733-742). Previously, we reported that migration of CD34⁺ cells in response to SDF-1 is significantly impaired in diabetics.[17] Since TGF-β-1 is known to down-regulate SDF-1 and its receptor CXCR4 (Wright N, de Lera T L, Garcia-Moruja C, et al. Transforming growth factor-beta1 down-regulates expression of chemokine stromal cell-derived factor-1: functional consequences in cell migration and adhesion. Blood. 2003; 102:1978-1984), we asked whether blockade of TGF-β would stimulate migration of these cells in response to SDF-1. We observed, as we have previously (Segal M S, Shah R, Afzal A, et al. Nitric oxide cytoskeletal-induced alterations reverse the endothelial progenitor cell migratory defect associated with diabetes. Diabetes. 2006; 55:102-109), that diabetic CD34⁺ EPCs migration was significantly lower than that of non-diabetic cells. Blockade of endogenous TGF-β1 expression enhanced migration in both diabetic (p<0.05) and nondiabetic cells (p<0.01) compared to control-PMO treated cells (FIG. 7).

To further characterize this effect, we examined expression of CXCR4 mRNA and protein following PMO treatment. Unexpectedly, in normal CD34⁺ EPC, expression of CXCR4 mRNA was increased after treatment with control-PMO suggesting that CXCR4 expression changes over time under these experimental conditions compared to the cells incubated with medium alone (P<0.05). Moreover, CXCR4 mRNA was significantly decreased with blockade of TGF-β1 compared to cells in medium alone (P<0.05) (FIG. 4A), In contrast, CXCR-4 expression in diabetic CD34⁺ cells was not changed by treatment with control-PMO, but was significantly increased in cells treated with anti-TGF-β-PMO (P<0.001).

We next evaluated the surface expression of CXCR4 receptor in CD34⁺ cells after PMO treatments. As shown in Table 1, the percentage of cells that are positive for CXCR4 increased significantly over the treatment period, regardless of the blockade of TGF-β1, or the cell origin (non-diabetic and diabetic cells).

Figure 8:
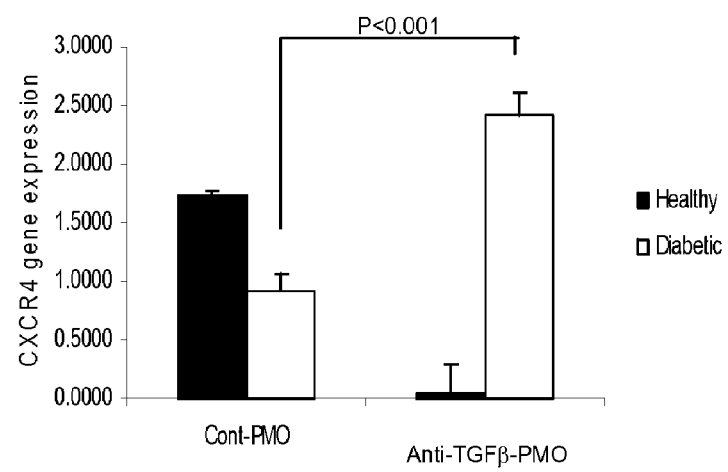
FIG. 8: Effects of PMOs on mRNA expression of CXCR4 and CXCR7 receptors in $CD34^+$ EPCs: Expression was quantified by real-time PCR and results were normalized to the expression of β-actin. Treatment with control-PMO caused an increase in CXCR4 expression in non-diabetic $CD34^+$ cells compared to that in medium-treated cells ($P<0.05$), but not in diabetic cells. Treatment with anti-TGF-β-PMO caused down-regulation of CXCR4 expression in non-diabetic cells ($P<0.05$), whereas the expression was up-regulated in diabetic cells ($P<0.001$) compared to that in control-PMO.
Figure 8:
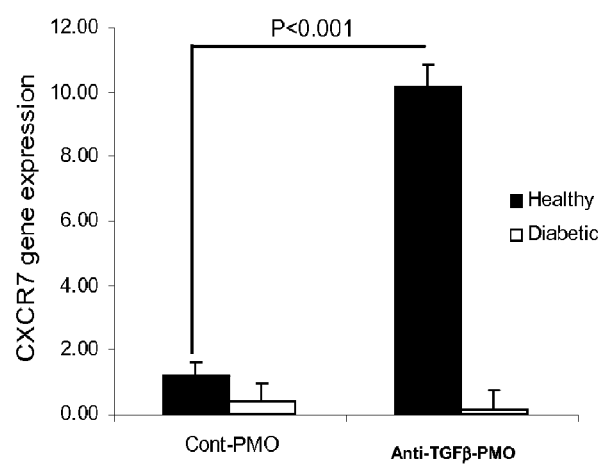

These unanticipated results lead us to ask whether anti-TGF-β-PMO treatment alters the expression of CXCR7, a recently identified second receptor for SDF1 (Sierro F, Biben C, Martinez-Munoz L, et al. Disrupted cardiac development but normal hematopoiesis in mice deficient in the second CXCL12/SDF-1 receptor, CXCR7. Proc Natl Acad Sci USA. 2007; 104:14759-14764). CXCR7 was initially identified as an orphan G-protein-coupled receptor receptor, RDC1, and recently de-orphanized and renamed as CXCR7 (Balabanian K, Lagane B, Infantino S, et al. The chemokine SDF-1/CXCL12 binds to and signals through the orphan receptor RDC1 in T lymphocytes. J Biol. Chem. 2005; 280:35760-35766; Burns J M, Summers B C, Wang Y, et al. A novel chemokine receptor for SDF-1 and I-TAC involved in cell survival, cell adhesion, and tumor development. J Exp Med. 2006; 203:2201-2213). Real-time PCR studies revealed that mRNA expression of CXCR7 was increased by the blockade of TGF-β1 only in the non-diabetic CD34⁺ cells (P<0.001) but not in the diabetic cells (FIG. 8B).

Example 3

Blockade of Endogenous TGF-β1 Increases NO Generation in Diabetic CD34⁺ EPCs in Response to SDF-1

Adequate intracellular levels of NO are critical for the migration of CD34⁺ EPCs (Segal M S, Shah R, Afzal A, et al. Nitric oxide cytoskeletal-induced alterations reverse the endothelial progenitor cell migratory defect associated with diabetes. Diabetes. 2006; 55:102-109; Aicher A, Heeschen C, Mildner-Rihm C, et al. Essential role of endothelial nitric oxide synthase for mobilization of stem and progenitor cells. Nat. Med. 2003; 9:1370-1376). Since we observed significant beneficial effect on migration of both non-diabetic and diabetic cells by the blockade of TGF-β1, we wanted to investigate whether this effect is associated with changes in NO release. We first examined NO release in response to SDF-1 in CD34⁺ cells treated with different PMOs. The signal transduction pathway involved in the release of NO by SDF-1 in CD34⁺ cells has not been elucidated. We, therefore, used different pharmacological inhibitors to delineate the pathway in CD34⁺ cells from non-diabetic subjects.

Figure 9:
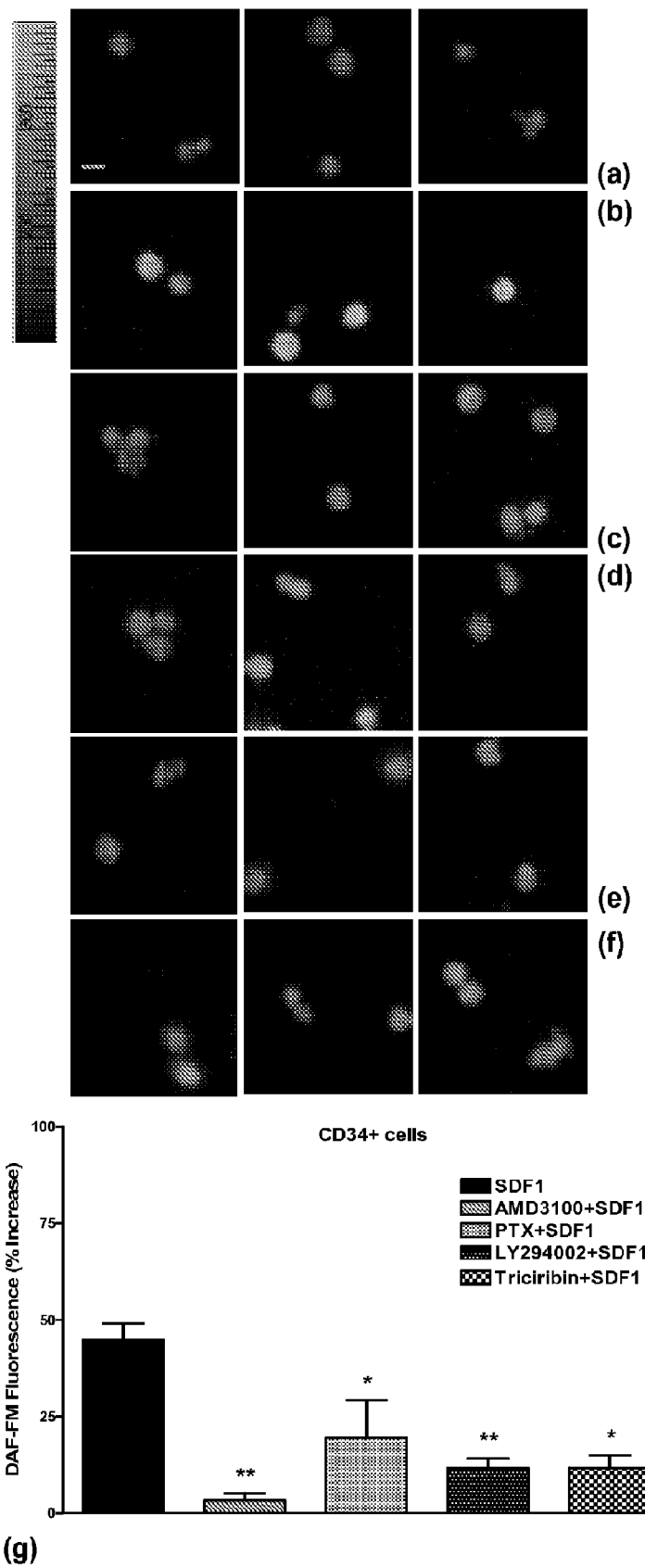
FIG. 9: Signalling pathway involved in NO release by SDF-1 in $CD34^+$ EPCs: NO release in non-diabetic $CD34^+$ cells was evaluated by DAF-FM fluorescence imaging. NO release in response to SDF-1 was evaluated in the absence and presence of different pharmacological inhibitors. Panels (a)-(f) show representative images of DAF-FM fluorescence with no (a) treatment (time-control) or (b) after treatment with 100 nM SDF-1 in the absence of pharmacological blockers or in the presence of (c) 10 µM AMD3100 or (d) 100 ng/mL pertussis toxin or (e) 20 µM LY294002 or (f) 20 µM triciribin. On the left is a color scale for DAF-FM fluorescence. (g) Summary of the effects of different pharmacological treatments on SDF-1-mediated NO release expressed as percent increase compared to the time-control. Significant reduction in the NO-release was observed after treatment with AMD3100 ($P<0.001$), pertussis toxin ($P<0.01$), LY294002 ($P<0.001$) or triciribin ($P<0.01$).

SDF-1 (100 nM) increased NO generation by 45±4% (n=4, FIG. 9). NO release by SDF1 levels was significantly decreased when cells were pre-treated with 10 μM AMD3100, a specific non-peptide antagonist of CXCR4 receptor (3±2%, P<0.001), or pertussis toxin, $G_i$-protein inhibitor (100 ng/ml, 20±9%, P<0.01), or LY294002, a phosphoinositide 3-kinase (PI3K) inhibitor (20 μM, 12±3%, P<0.001) or triciribin, an Akt inhibitor (30 μM, 12±3%, P<0.01) (FIG. 9). These results suggested that in CD34⁺ cells SDF-1-mediated NO release involves CXCR4/$G_i$protein/PI3K/Akt pathway.

Figure 10:
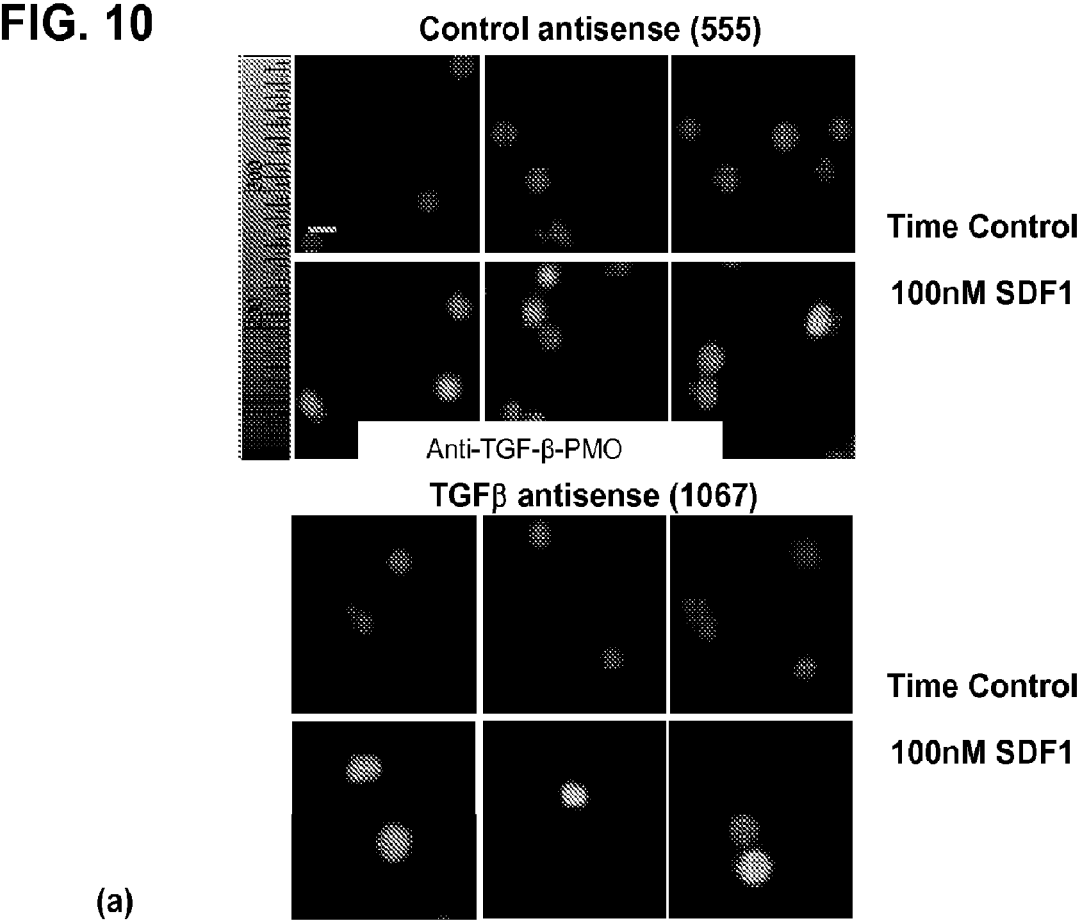
FIG. 10: Effects of PMOs on NO release by SDF-1 in non-diabetic and diabetic CD34$^+$ EPCs: NO release in response to SDF-1 was evaluated by DAF-FM fluorescence imaging in non-diabetic and diabetic cells after treatment with control or anti-TGF-β-PMO. (a) Representative DAF-FM fluorescence images of non-diabetic cells after treatment with control or anti-TGF-β-PMO and stimulated with 100 nM SDF-1. Shown in the left was colour scale for DAF-FM fluorescence. (b) Summary of the effects of PMOs on SDF-1-mediated NO release in non-diabetic cells expressed as percent of time-control. NO release was similar after treatment with control or anti-TGF-β-PMOs. Panels (c)-(h) Representative DAF-FM fluorescence images of diabetic CD34$^+$ cells after treatment of PMOs and stimulated with SDF-1 in the absence or presence of pharmacological blockers. Control-PMO treated cells: (c) and (d) time-control and SDF-1-stimulated cells, respectively. Cells treated with anti-TGF-β-PMO (e) time-control, (f) SDF-1 stimulated, (g) SDF-1-stimulated in the presence of 10 µM AMD3100 and (h) SDF-1-stimulated in the presence of 100 ng/mL pertussis toxin. On the left is a color scale for DAF-FM fluorescence. (i) Summary of the effects of PMOs and pharmacological treatments on NO release by SDF-1. NO release is significantly higher in diabetic cells treated with anti-TGF-β-PMO compared to control-PMO ($P<0.0001$). Increased NO release by SDF-1 in diabetic cells after anti-TGF-□-PMO treatment was significantly decreased by AMD3100 ($P<0.01$) and pertussis toxin ($P<0.01$).
Figure 10:
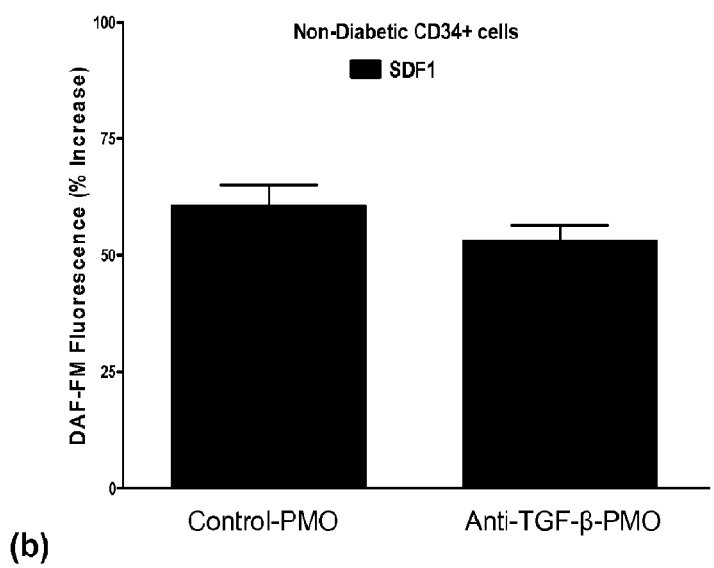
Figure 10:
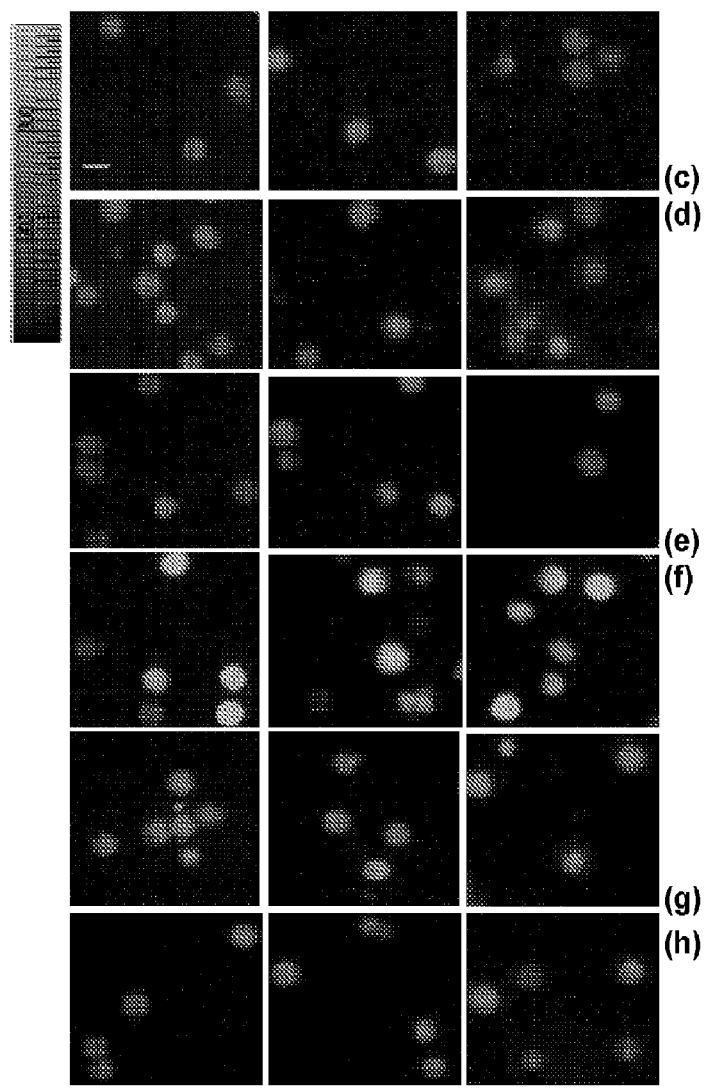
Figure 10:
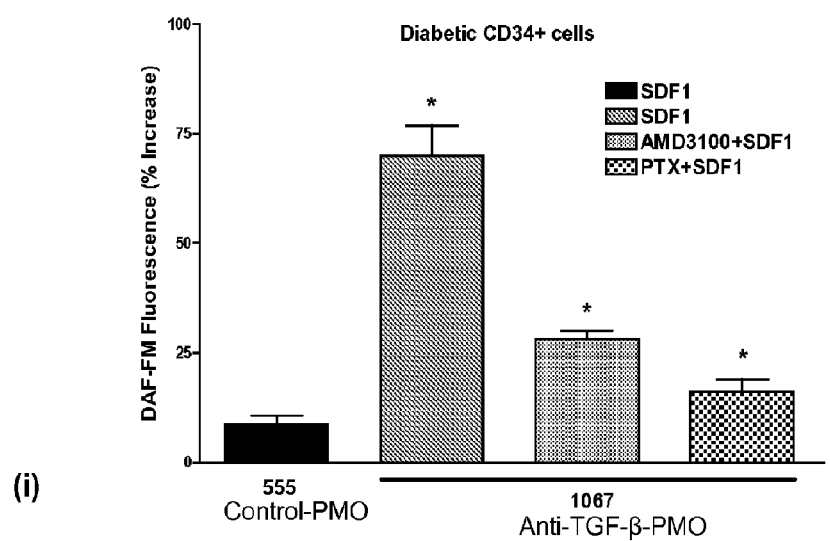

We then studied whether pre-treatment with control or anti-TGF-β-PMO (40 μg/mL) influenced NO release in these cells. CD34+ cells derived from non-diabetic subjects pre-treated with control-PMO or anti-TGF-β-PMO showed NO-release in response to SDF-1 to a similar extent, i.e. 60±5% and 54±4% (n=3) (FIG. 10A and FIG. 10B), respectively. In marked contrast, diabetic CD34+ cells treated with anti-TGFβ-PMO showed a marked increase in NO generation (69±7%, n=4, p<0.0001) compared to control-PMO (9.2% n=4) (FIG. 10C-6F and 10I). The restored NO-release in diabetic cells following treatment with anti-TGFβ-PMO was significantly decreased by AMD3100 (28±2%, P<0.01) or pertussis toxin (16±3%, P<0.01) (FIG. 10G-6H and 10I), suggesting the CXCR4 receptor activation in this response.

Example 4

Figure 11:
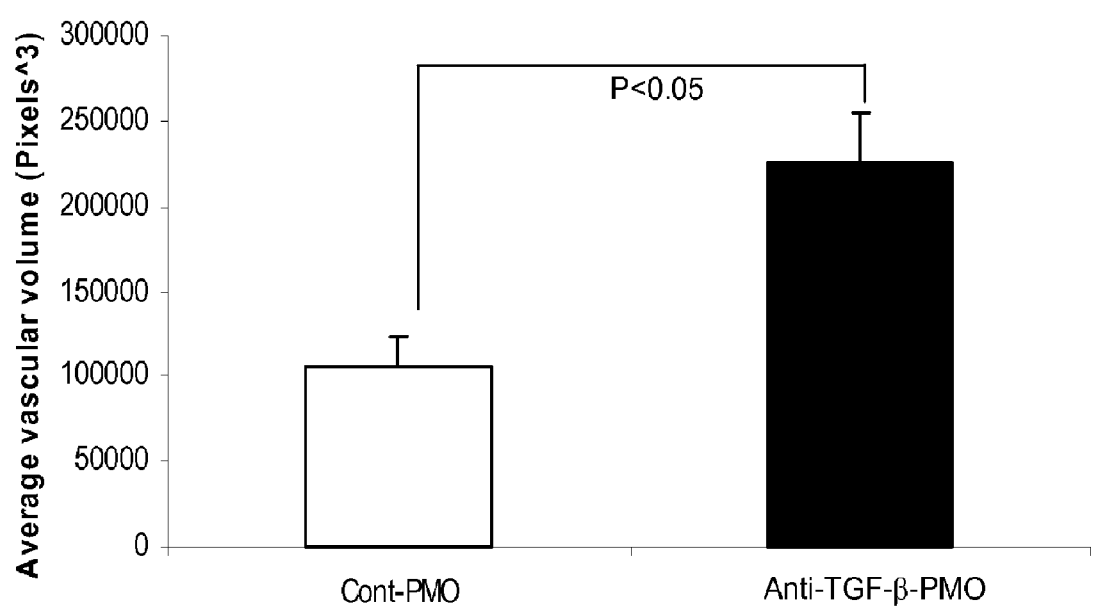
FIG. 11: TGF-β1-PMO treatment of HSC increases homing to areas of laser injury in the retina. Morphometric analysis showing increase in recruitment of HSC to sites of laser injury following adoptive transfer of HSC that underwent overnight blockade of endogenous TGF-β with TGF-β1-PMO vs control PMO, *$p<0.05$.

Blockade of Endogenous TGF-β by anti-TGF-β-PMO Increases Homing of Murine HSCs to CNV Lesions To determine whether TGF-β blockade would improve stem cell homing to damaged retina, we used a laser injury model. As shown in FIG. 11, pre-treatment with TGF-β-PMO caused a substantial increase in the numbers of GFP+ HSCs that were recruited to the laser injury site. Thus, the TGF-β-PMO treatment of HSCs resulted in the cells homing to the injury site more than control-PMO treated cells (p<0.05) or cells exposed to medium alone.

Example 5

Figure 12:
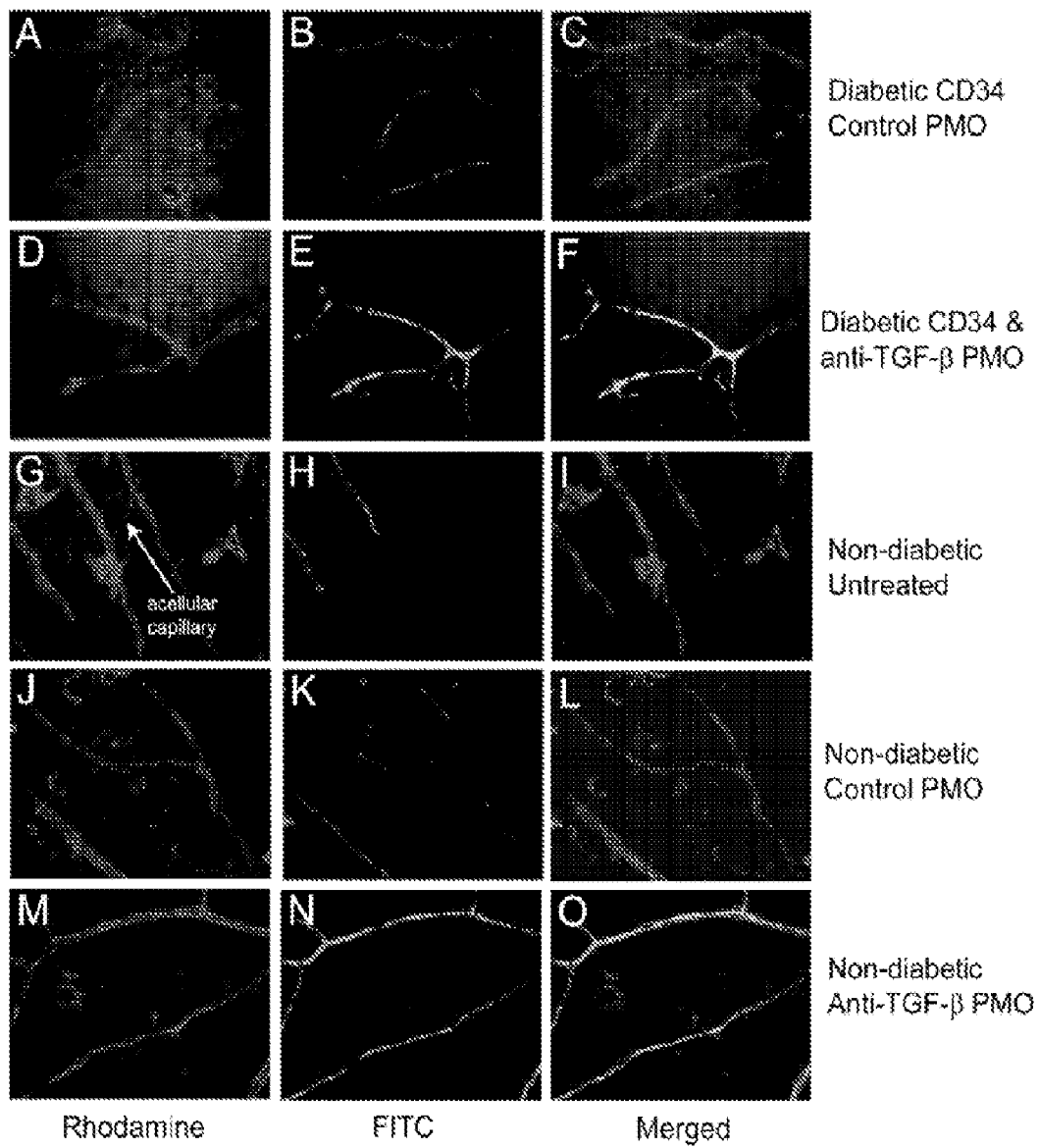
FIG. 12: Anti-TGF-β-PMO treated HSCs integrate into degenerate vasculature in mouse eyes damaged by I/R injury. (A) HSCs pre-treated with anti-TGF-β-PMO or control-PMO injected intravitreally showing incorporation in retinal ischemic vasculature. HSCs show a substantial increase in incorporation in the group pre-treated with anti-TGF-β-PMO. (B) Morphometric quantification of incorporated HSCs expressed in terms of average fluorescence intensity per 100 mm$^2$ field.

Blockade of Endogenous TGF-β in CD34+ EPCs Increases Vascular Repair in Retinal I/R Injury Model Acute exposure of hydrostatic pressure to the anterior chamber of eye causes profound ischemic response and leads to capillary degeneration (formation of acellular capillaries; white arrow, FIG. 12). These lesions are also the pathological hallmark of retinopathic ischemic injury in diabetes. EPCs pre-treated with anti-TGF-β-PMO showed profound homing to areas of ischemic injury as compared to CD34+ EPCs treated with control-PMO (FIG. 12). To further quantify HSC incorporation individual confocal images were analysed for FITC immunoreactivity per 100 μm$^2$ area. Pre-treatment of EPCs with anti-TGF-β-PMO resulted in 2.5 fold increase in incorporation of these cells to injured retinal capillaries, as compared to the pre-treatment with control-PMO (P<0.001). Diabetic CD34+ cells treated with control-PMO showed essentially no repair as these cells are defective and unable to migrate or participate in re-endothelialzation of acellular capillaries. In marked contrast, pretreatment of diabetic cells with anti-TGF-β-PMO results in a robust reparative response with restoration of the defective cells ability to repair acellular capillaries.

Materials and Methods for Examples 1-5
Methods
Isolation of Human CD34+ EPCs

Human cord blood and bone marrow CD34+ EPCs were purchased from AllCells (Emeryville, Calif.) as positively selected lin−, magnetic bead-purified frozen cell populations that were >95% CD34+ cells by FACS analysis. Cells were thawed in a 37° C. water bath, diluted in excess IMDM 10% FBS, pelleted by centrifugation (300×g for 10 min), washed by centrifugation one additional time and, finally, counted using a hemocytometer. Viability, as determined by trypan blue dye exclusion, was routinely >95% after thaw and washes.

Further purification was carried out prior to survival and proliferation studies. Cells were adjusted to 5×10$^5$/mL in phosphate-buffered saline (PBS) containing 2% (v/v) fetal bovine serum (FBS) and incubated with single murine antibody controls and murine anti-CD34-PE, anti-CD45-PE-Cy5 and anti-CD38-APC. Just prior to cell sorting, propidium iodide (2 μg/mL) was added to detect non-viable cells. CD34+, CD45$^{mid}$ cells (HSCs are CD45$^{mid}$ expressing and can be clearly separated from contaminating lymphocytes, which are CD45$^{high}$ expressing) and CD38$^{+/-}$ cells were directly sorted into 96-well round bottom plates (10±2 cells/well) containing IMDM, 10% horse serum, 10% FBS, 100 units/mL of penicillin, 10 μg/mL streptomycin, 20 mM 1-glutamine and 1 μM hydrocortisone±PMOs. At day 5, a hematopoietic growth factor cocktail (Hgf-cocktail) consisting of 20 ng/mL thrombopoietin, 50 ng/mL stem cell factor, 50 ng/mL interleukin-3 and 20 ng/mL interleukin-6, all purchased from PeproTech, N.J., was added to the wells. Cells were followed by daily direct light microscopy (×200) to assess cell proliferation. Cells that proliferated in response to growth factors were scored as cells that survived after the 5-day period in the absence of growth factors.

CD34+ CD45$^{mid}$ cells were also isolated from diabetic and non-diabetic patient peripheral blood and tested in the survival and proliferation assays as described above. Briefly, 20 mL of fresh blood was collected according to IRB-approved protocols in heparinzed tubes, diluted 1:1 in PBS with 2% FCS, and layered over 1.077 g/mL LymphoPrep (Greiner bio-one, NC), and centrifuged for 20 min at 400×g. Low density mononuclear cells were harvested and then incubated with lineage-specific antibodies (StemCell Technologies, Vancouver, BC) for 15 mM, followed by magnetic microbeads to bind lineage positive cells. After magnetic separation, lin− cells were incubated with anti-CD34-PE, anti-CD45-PE-Cy7 and ±CD38-APC antibodies (BD PharMingen, San Diego Calif.) plus single positive controls and isotype control antibodies as described above, sorted by FACS, and subjected to the same conditions for survival and proliferation studies described above.

Isolation of Murine HSCs

HSCs were harvested from the bone marrow obtained from femurs and tibiae of mice homozygous for GFP$^2$. Fluorescently labelled c-kit (CD117) and Sca-1 (both from BD PharMingen, San Diego, Calif.) were used to select enriched HSC from mononuclear cell fractions using a BD cell sorter (FACS Calibur-Flow Cytometer, BD Bioscience, San Jose, Calif.). We have previously shown using this technique that this produces a 95% pure hemangioblast cell/HSC cell population[4]

TGF-β Blockade Ex Vivo Just Prior to In Vivo Administration

Anti-TGF-β-PMOs for or control-PMOs (AVI-Biopharma, Portland, Oreg.) were designed and synthesized as a lyophilized powder and initially dissolved in sterile distilled water and serially diluted. Optimal sequences were chosen empirically by testing in both in vitro and in vivo assays The control-PMO sequence was 5' CGT TCT GAT AGC TGT ACC TC 3' (SEQ ID NO: 1) (AVI BioPharma, sequence ID#0-1-0-555) while anti-TGF-β-PMO sequence was 5' GAG GGC GGC ATG III GAG GC 3' (SEQ ID NO: 2) (AVI BioPharma, sequence ID#0-1-01067). Control- or anti-TGF-β-PMOs were subsequently diluted in RPMI to produce a stock solution. We tested varying concentrations of PMOs from 40-320 μg/mL.

CD34$^+$ EPCs were isolated from cord blood, human bone marrow and peripheral blood as described above and sorted 10 cells per well in a 96 well plate in either the presence or absence of growth factors and in presence or absence of anti-TGFβ-PMO. Cells were incubated overnight at 37° C. in IMDM containing 10% horse serum, 10% FBS, 100 units/mL of penicillin, 10 µg/mL streptomycin, 20 mM 1-glutamine and 1 µM hydrocortisone with PMOs or control. This incubation period was previously determined by measuring the uptake of fluorescein isothyocyanate (FITC)-labelled PMOs in HSCs.

Migration Assay

Cell migration following overnight blockade with anti-TGF-β-PMOs or control-PMO treatment was performed using a modified Boyden chamber assay as described previously.[11] Briefly, anti-TGF-β—or control-PMO-treated murine HSCs were incubated with 6 µg/mL of calecin for 30 min. Migration of cells to the gradient of SDF-1 was studied across 5 µM pore membrane (Neuroprobe Labtek Gaithersburg, Md.). Each sample was loaded in triplicate. RPMI alone or RPMI with 20% FBS served as negative and positive controls, respectively. The fluorescence intensity of migrated cells was measured using plate reader (Biotek Synergy2).

Quantitative Real-Time PCR

Total mRNA from CD34 cells was isolated by using the Total RNA Mini Kit (Bio-Rad, Hercules, Calif.). The mRNA was transcribed by using an iScript cDNA Synthesis Kit (BioRad), and real-time PCR was performed using primers for CXCR4, CXCR7, or beta actin as per manufacturer's instructions (Ambion, Austin, Tex.). Real-time PCR was performed on 7500 Fast Real-Time PCR system for 40 cycles and all reactions were performed in triplicate.

Determination of NO Production by DAF-FM Fluorescence Imaging

Human CD34$^+$ EPCs were incubated overnight with either control-PMO or anti-TGF-β-PMO at a concentration of 40 µg/mL. NO production was quantified in human peripheral blood-derived CD34$^+$ cells using NO-sensitive cell-permeant fluorescent dye DAF-FM. CD34$^+$ EPCs were loaded with 20 µM DAF-FM diacetate (Invitrogen) in 500 µl, of DPBS (MediaTech. Inc.) with glucose (1 mg/mL) and L-arginine (1 mM). SDF1 (100 nM) was added to the cell suspension 15 minutes after the addition of DAF-FM. Pharmacological inhibitors were added 30 min before the addition of DAF-FM. Cells were incubated for 3 h after the SDF 1 addition. Cells were washed (4×) and 75 µL of cell suspension was placed in the coverslip-bottomed dish for fluorescence imaging. Fluorescent images were obtained using a computer-controlled monochromator excitation light source (TILL Polychrome II, TILL-Photonics, Martinsried, Germany) and a cooled CCD camera with exposure control (SensiCam, Till-photonics). During excitation at 488 nm with 50 ms of exposure time, emission at 510 nm was collected by the camera at 2×2 binning and images were acquired by Till-Vision software (Till Photonics, Martinsried, Germany). Images were corrected for background and maximum fluorescence intensity in individual cells was quantified in terms of arbitrary fluorescence units using Till-Vision software. Changes in fluorescence with different treatments were expressed as percent change with respect to cells that were used as time/vehicle control i.e. cells received no treatments but loaded with DAF-FM. Up to 75 numbers of cells were imaged per sample/donor and 'n' denotes number of donors used.

Animal Studies

All animal studies were approved by the institutional animal care and use committee and studies were conducted in accordance with The Guiding Principles in the Care and Use of Animals (NIH), and the ARVO Statement for the Use of Animals in Ophthalmic and Vision Research. Healthy C57BL/6J mice were obtained from Jackson Laboratory (Bar Harbor, Me.) and housed in our institutional animal care facilities. Transgenic mice homozygous for GFP (C57BL/6-Tg(UBC-GFP)30Scha/J) were also obtained from Jackson Laboratory. At study termination, the animals were killed by overdose of ketamine and xylazine (14 and 30 mg/Kg, respectively) and the eyes were removed for immunonohistochemical processing.

CNV Lesion as a Model of Injury and Repair by Murine HSCs

In order to generate discrete areas of injury, we induced choroidal neovascularization by laser rupture of Bruch's membrane as previously described.[12,13] Briefly, anesthetized GFP$^+$ bone marrow chimeric mice were subjected to three applications of argon green laser light with a wavelength of 532 nM, power of 150 mW, duration of 100 ms and spot size of 50 µm., placed in three quadrants of the choroid, approximately one optic disc diameter in distance from the optic disc. This treatment foHns a "bubble" as Bruch's membrane ruptures from the energy of the laser application, resulting ultimately in choroidal neovascularization and anastomoses that can be clearly visualized against the backdrop of the surrounding intact retinal pigmented epithelium. Thus, discrete and bounded areas of neovascularization can be easily quantified.

To assess the effect of TGF-β-PMO blockade on the ability of murine HSCs to contribute to CNV and the nature of that contribution, adoptive transfer was used. Prior to inducing the laser injury, bone marrow HSCs were isolated from GFP$^{+/+}$ donor mice as described earlier. After overnight incubation with vehicle (RPMI), control- or anti-TGF-β-PMO, the HSCs were resuspended in sufficient PBS to ensure a concentration greater than or equal to 10,000 cells/100 µL and 100 µL of this suspension was then injected into the retro-orbital sinus of each mouse (n=12 for each condition). The injection was performed immediately following laser injury. Mice were euthanized two weeks after induction of CNV and adoptive transfer of pre-treated HSCs.

Assessment of CNV Lesions and HSC Contribution.

The eyes were enucleated and then fixed with 4% paraformaldehyde for 1 h, after which they were dissected to remove the cornea, lens, vitreous and neural retina. The resulting posterior cups—consisting of the RPE, the underlying choroid, and the sclera—were permeabilized by incubation overnight at 4° C. in HEPES buffer with 0.2% Triton X-100, and the were then reacted overnight with rhodamine-conjugated *R. communis* agglutinin I (Vector Laboratories, Burlington, Calif.) in order to stain the vasculature within the choroidal lesions. The posterior cups were mounted flat by four radial cuts and then digital image captures were made using a confocal microscope (BioRad MRC 1024, BioRad Corporation, Temecula, Calif.).

Captured digital images were evaluated morphometrically using ImageJ software (Research Services Branch, National Institutes of Health, Bethesda, Md.). Confocal z-series image captures of the red and green channels were analyzed as follows: 1) a calibration for the specific objective and microscope was applied to set the pixel-to-length ratio; 2) a threshold was applied using the Otsu algorithm; 3) images were made binary; 4) a region-of-interest (ROI) was outlined to include the entire lesion area; 5) a particle analysis was performed to quantify the pixel area above the threshold level within the ROI. The sum of lesion area throughout the z-series was then multiplied by the z thickness (typically 4 µm) to obtain the lesion volume. Lesion volumes for each animal are then averaged and treated as an n of 1 for statistical analysis. Changes in lesion volume among treatment groups are determined by averaging the mean lesion volume for all animals in a treatment group, and reported as mean±standard error from the mean. Comparisons are tested for statistical significance by Student's t-test or one-way analysis of variance (ANOVA). Differences in lesion volume with a p value less than or equal to 0.05 were considered significant for subsequent quantitative volumetric analysis.

Acute Vascular Injury: Ischemia-Reperfusion Model

Mice (n=20) were kept under inhalation anaesthesia (isoflurane vapor) during induction of ischemia. The anterior chamber of the eye was cannulated with a 30-gauge needle attached to an infusion line of sterile saline, and the eye was subjected to 2 h of hydrostatic pressure (80-90 mmHg, measured by TonoPen; Medtronic Solan, Jacksonville, Fla.). This resulted in retinal ischemia as confirmed by whitening of the iris and loss of the red reflex. After 2 h, the needle was withdrawn and the intraocular pressure was normalized, which resulted in the reperfusion injury. The contralateral eye served as a control.

Seven days after the insult, at which time retinal capillary damage was appreciable,[14,15] the animals were injected intravitreally with isolated human $CD34^+$ EPCs pre-treated with either anti-TGF-μ-PMO or control-PMO. After 48 h the animals were euthanized, the eyes were enucleated and the neural retinas were isolated by dissection. The retinas were permeabilized as described above, and reacted with rhodamine-conjugated *R. communis* agglutinin I. To assess the location of the injected human $CD34^+$ EPCs, retinas were further incubated with mouse monoclonal anti-human nuclear antigen (Chemicon) followed by secondary staining with FITC-conjugated goat-anti-mouse IgG antibodies (Chemicon). Confocal images of six random fields were taken and fluorescence intensity in each 100 $\mu m^2$ was analysed using ImageJ software. Appropriate non-immune antibodies, as well as incubation without primary antibody, were used to determine background and non-specific antibody binding.

Example 6

CD34+ Cells Subject to TGF-β Blockade Adhere to Endothelial Cells

The inventors believe that a transient TGF-β blockade in diabetic and normal $CD34^+$ and CD 34-/EPCs will increases their proliferation rate, increase their ability to form capillary tubes, and increase their adherence to endothelial cells. To test this hypothesis, lin-$CD34^+$ and lin-CD34− cells are used in a series of in vitro assays including adherence of to vascular endothelial cells, cell proliferation, and cell capillary tube formation on fibronectin.

The inventors have recognized that anti-TGF-β treatment of murine and human stem cells increases hematopoietic stem cell engraftment. As discussed above, the inventors have shown that anti-TGF-β treatment of CD34+ cells can increase migration towards SDF-1 by increasing expression of the cell surface receptor for SDF-1, CXCR-4. Blocking endogenous TGF-β corrects the decreased proliferation rate observed in these precursor cells from diabetic patients. Furthermore, EPC adherence at sites of vascular injury is critical for vascular repair and in vitro diabetic $CD34^+$ cells have reduced adherence compared to non-diabetic healthy cells. Accordingly, the adherence of diabetic $CD34^+$ cells to endothelial monolayers is measured and it is determined whether pre-treatment with anti-TGF-β PMO enhances adherence and, in turn, enhances the reparative function of these cells. A "gold standard" assay of in vitro angiogenesis is the tube formation assay. Diabetic EPC have reduced ability to form tubes in vitro,[35] so the inventors evaluate whether anti-TGF-β treatment correction of this defect and improvement of tube formation towards that observed with non-diabetic cells.

Methods:

Isolation of $CD34^+$ cells: Blood is collected by routine venipuncture into CPT™ tubes with heparin (BD Biosciences, Franklin Lakes, N.J.). The cells are processed into lin-cells, then the $CD34^+$ cells are positively selected using autoMACS™ (Miltenyi Biotec Inc.) resulting in a lin-CD 34− and CD+ population.

TGF-β1 ELISA: A variation of an ELISA to detect active and total TGF-β1 as previously published is utilized.

TGF-β blockade: Isolated lin-$CD34^+$ and lin-CD 34− cells are incubated for 8 hrs at 37° C. in a $CO_2$ incubator with 25 μM TGF-β PMO, 25 μM scrambled oligonucleotide, or medium alone, after which they are washed 3× by centrifugation (300×g, 10 min) in basal medium.

Microvascular endothelial cultures: Human retinal endothelial cells (HREC) are isolated from cadaveric retinas and maintained as previously described[58]. Macrovascular endothelial cell cultures: Human aortic endothelial cells (HAEC) (Cambrex Corporation, East Rutherford, N.J.) will be cultured in EBM-2 medium (Cambrex Corporation) and passages 3-5 are used for these studies.

$CD34^+$ cell adhesion to endothelial cells: 24-48 hr prior to the assay, either HAEC or HREC are suspended in EGM-2 (Cambrex, Walkersville, Md.) and seeded onto a 24 well plate and cultured until a monolayer is formed. CD34 cells isolated and treated as above are vitally labeled with DiI-acetylated LDL (Molecular Probes), washed, and resuspended in PBS with 10% fetal bovine serum. One thousand cells from either group contained in 25 μl will be added to each well. The same number of $CD34^+$ cells are added to wells without endothelial cells, serving as a control for non-specific binding. After a 4 hr incubation period, non-attached $CD34^+$ cells are removed by aspiration and the monolayers and control wells are washed 2× with 1 ml of PBS. Adherence is measured in a Bio-Tek FL600 fluorescent plate reader (Bio-Tek Instruments) at excitation/emission wavelengths of 485/530.

Tube formation assay: is performed as previously described.[59] Briefly, freshly isolated lin-$CD34^+$ and lin-CD34− cells from healthy controls or diabetic individuals are immediately treated as described above and, then cultured on fibronectin coated plates for 3 days in EndoCult™ Medium (StemCell Technologies) before being trypsinized and split into wells of a 24-well plate.

Example 7

TGF-B Blockade Will Enhance Their Reparative Function $CD34^+$ cells have been shown to repair damaged endothelium in a variety of animal models. Cellular therapy resulted in functional improvement similar to that previously described utilizing other endothelial precursor populations. Adoptive transfer of $CD34^+$ cells has previously been shown to restore blood flow and increase capillary density, decreasing limb loss and facilitating recovery from myocardial injury. Infarction models in the mouse have a high mortality and it is difficult to perform functional studies. The inventors postulate that a transient TGF-β blockade in $CD34^+$ and CD 34−/EPCs enhances their reparative function by facilitating their homing to areas of cardiac ischemia in the injured heart and generate reparative endothelial cells. To test this hypothesis, the inventors use the adoptive transfer technique to deliver modified lin–CD34+ and lin–CD34– cells from Caucasians and African Americans with type II diabetes transplanted into a nude rat myocardial infarction model.

Methods

Animals: Nude rats are purchased from Jackson Labs.

TGF-β blockade and vital labeling is conducted as described for Example 6.

Human CD34+ cell isolation: isolation is carried out as described for Example 6.

Myocardial infarction and transplantation: myocardial ischemia is induced by ligation of the left coronary artery as described previously.[64] Fifteen minutes after infarct the pretreated and labeled cells ($3 \times 10^5$ per animal) are injected into the ischemic and peri-ischemic myocardium.

Four weeks after induction of myocardial ischemia the animals are euthanized and their cardiac tissue removed and preserved by immersion fixation in buffered 4% paraformaldehyde. The cardiac tissue is examined by immunohistology to assess the degree of repair of the infarcted tissue. Fluorescence microscopy is used to determine the degree to which human EPC have incorporated into the rat tissue. The rat tissue is reacted with human-specific antibody to endothelium (clone PAL-E, Abcam, Cambridge, Mass.) to detect endothelial cells of human donor origin.

Example 8

Treatment of Diabetic Ulcers with Treated HSCs

Generally, when the skin of an individual is torn, cut or punctured (wounded), the body naturally reacts to regenerate dermal and epidermal tissue to close the wound. The wound regeneration process typically includes a set of complex biochemical events that take place in a closely orchestrated cascade to repair the damage. These events overlap in time, but may be categorized into different phases, namely the inflammatory, proliferative, and remodeling phases.

In the inflammatory phase, bacteria and debris are phagocytized and removed, and factors are released that cause the migration and division of cells involved in the proliferative phase. In the proliferative phase, the principal steps include angiogenesis, fibroplasias, granulation tissue formation, epithelialization, and wound contraction. Angiogenesis involves the development of new capillary blood vessels for the wound area to provide oxygen and nutrients to the healing tissue. In fibroplasias and granulation tissue formation, fibroblasts grow and form a new, provisional extracellular matrix (ECM) by excreting collagen and fibronectin. In epithelialization, epithelial cells migrate across the wound bed to cover the bed. In contraction, the wound is made smaller by the action of myofibroblasts, which establish a grip on the wound edges and contract themselves using a mechanism similar to that in smooth muscle cells. When the cells' roles are close to complete, unneeded cells undergo apoptosis.

It is known that a number of disease states hinder the normal wound healing process. For example, individuals with diabetes often experience problems with what are termed "diabetic foot ulcers." Diabetic foot ulcers are sores or wounds, typically, on the feet that typically occur in individuals having diabetes. Oftentimes, these diabetic ulcers occur as a direct or indirect result of nerve damage in the feet of the individual as the prolonged high blood sugar and insulin levels associated with diabetes is linked with damage to the nerves in the feet. Such nerve damage in the feet, referred to as peripheral neuropathy, can cause loss of sensation as well as cause deformities of the feet. Due to the loss of sensation, individuals with peripheral neuropathy may hurt their feet by repetitive minor trauma (e.g., by prolonged walking) or a single major trauma (e.g., by scraping skin, stepping on objects, immersing feet in hot water, cutting toenails inappropriately, or wearing ill-fitting shoes), but nevertheless may not notice such injuries. A further complication of diabetes is a reduction in blood flow to the feet due to the arterial blockage or other causes, thereby severely inhibiting the body's ability to adequately provide complete the proliferative stage of wound regeneration/healing described above. As a result, once the skin of the foot is torn, cut, or punctured, the wound healing process (e.g., the proliferative phase) may be inordinately slow in repairing the wound. Further, once a serious wound develops, the risk of infection is high as the individual's body is simply unable to heal the wound. Even further, once infection starts, the infection may be very difficult to reverse, and amputation of the affected limb is common.

A number of treatments have been proposed to speed wound healing in patients having diabetic ulcers. These treatments include the use of skin grafts or "tissue equivalents." Tissue equivalents involve the isolation of replacement skin cells that are expanded and seeded onto or into a supporting structure, such as a three-dimensional bio-resorbable matrix, or within a gel-based scaffold. Both skin grafts and tissue equivalents are notably complex and, especially in the case of reduced blood flow to the patient's feet, are often unsuccessful.

In view of the inventors' discoveries of the improved healing potential of HSCs as treated according to the teachings herein, the inventors have recognized that the treated HSCs may be utilized in the treatment of topical wounds. Thus, according to another embodiment, the invention pertains to an improved method of treating diabetic ulcers by administering treated HSCs to a patient experiencing diabetes related lesion or wound. In a more specific embodiment, there is provided a method of treating a wound in a patient comprising administering topically an effective amount of treated HSCs to the wound.

In accordance with yet another aspect of the present invention there is provided a method of treating a wound in a patient comprising administering parenterally an effective amount of treated HSCs.

In accordance with yet another aspect of the present invention there is provided a method of treating a subject having a wound. The method comprises administering via topical administration a wound composition comprising an effective amount of treated HSCs in the vicinity of the wound, such that HSCs may migrate and adhere to the locations of the wound and/or surrounding areas. Surrounding areas would include healthy tissues contiguous to the wound.

In accordance with yet another aspect of the present invention, there is provided a method for treating a diabetic ulcer comprising administering to a patient in need thereof a wound composition comprising an effective amount of treated HSCs.

In accordance with yet another aspect of the present invention there is provided a method of ameliorating the progression of a wound in a subject comprising administering an effective amount of treated HSCs to the wound.

The term "wound" as used in this Example refers to any break in the epithelium. The break may have been induced from a cut, abrasion, adhesion, surgical incision, thermal, chemical, or friction burn, ulcer, or pressure, or the like, as a result of an accident, incident, surgical procedure, or the like. Wound can be further defined as acute and/or chronic. Compositions of the present invention have been found to be particularly useful in the treatment of diabetic ulcers.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

All references, including patent and non-patent literature, cited herein are incorporated by reference in their entirety.

TABLE 1

| Cell Surface Antigen | Normal MPB CD34 + CD45+ % of cells | | | Diabetic PB* CD34 + CD45+ % of cells | | |
| --- | --- | --- | --- | --- | --- | --- |
| | T = 0 | PMO 555 control | PMO 1067 Anti-TGFβ1 | T = 0 | PMO 555 control | PMO 1067 Anti-TGFβ1 |
| CXCR4 | 40.7 | 88.5 | 85.3 | 42.5 | 74.1 | 72.7 |
| CD14 | 85.3 | 69.3 | 73.3 | 85.5 | 59.3 | 62.4 |
| CD105 | 70.9 | 71.0 | 62.9 | 71.0 | 58.8 | 51.7 |
| VEGFR-2 | 71.3 | 62.9 | 56.5 | 71.7 | 59.3 | 62.4 |
| CD38 | 99.0 | 79.9 | 82.3 | 99.1 | 92.2 | 94.2 |

What is claimed is:

1. A method of treating vascular lesions in a subject in need thereof, said method comprising
procuring CD34+ stem cells from said subject to obtain procured hematopoietic stem cells;
treating said procured CD34+ stem cells, ex vivo, by blocking activity of TGF-β1 in said stem cells to obtain treated CD34+ stem cells;
administering said treated hematopoietic stem cells to said subject wherein said treated hematopoietic stem cells home to the vascular lesions in the subject, wherein said treated hematopoietic stem cells comprise enhanced homing ability compared to the hematopoietic stem cells at the procuring step.

2. The method of claim 1, wherein said treating comprises subjecting said procured CD34+ stem cells to an antisense nucleotide specific to an mRNA sequence encoding TGF-β1.

3. The method of claim 1, wherein said subject is diabetic.

4. The method of claim 1, wherein said vascular lesions are associated with diabetic retinopathy.

5. The method of claim 1, further comprising coadministration of a TGF-β blocking agent.

6. The method of claim 1, wherein said vascular lesions are associated with Retinal Vein Occlusion.

7. The method of claim 1, wherein said vascular lesions are associated with choroidal neovascularization.

8. The method of claim 1, wherein said administering occurs in response to a stroke in said subject.

9. The method of claim 1, wherein said administering occurs in response to myocardial infarction.

* * * * *